(12) United States Patent
Eyrard et al.

(10) Patent No.: US 9,527,627 B2
(45) Date of Patent: Dec. 27, 2016

(54) CONNECTOR FOR DIALYSIS CONTAINER, CONTAINER EQUIPPED WITH SUCH CONNECTOR, MANUFACTURING AND FILLING METHOD FOR SUCH CONNECTORS AND CONTAINERS

(75) Inventors: Thierry Eyrard, Lyons (FR); Philippe Laffay, Sainte-Foy-lès-Lyon (FR)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 329 days.

(21) Appl. No.: 14/110,399

(22) PCT Filed: May 11, 2012

(86) PCT No.: PCT/EP2012/058829
§ 371 (c)(1),
(2), (4) Date: Nov. 18, 2013

(87) PCT Pub. No.: WO2012/156331
PCT Pub. Date: Nov. 22, 2012

(65) Prior Publication Data
US 2014/0034657 A1    Feb. 6, 2014

Related U.S. Application Data

(60) Provisional application No. 61/487,468, filed on May 18, 2011.

(30) Foreign Application Priority Data

May 18, 2011    (FR) ...................... 11 54323

(51) Int. Cl.
*A61M 37/00*    (2006.01)
*B65D 25/38*    (2006.01)
(Continued)

(52) U.S. Cl.
CPC .............. *B65D 25/38* (2013.01); *A61J 1/1475* (2013.01); *A61J 1/1487* (2015.05);
(Continued)

(58) Field of Classification Search
CPC ... B65D 25/38; A61M 1/1656; A61M 1/1668; A61J 1/1475; A61J 1/10; A61J 1/1425; A61J 1/1487
(Continued)

(56) References Cited

U.S. PATENT DOCUMENTS 2,659,370 A    11/1953    Smith
4,048,999 A    9/1977    Köbel
(Continued)

FOREIGN PATENT DOCUMENTS

CA    2703134 A1    4/2009
CN    1336825 A    2/2002
(Continued)

OTHER PUBLICATIONS

Chinese Office Action dated Apr. 1, 2015 in counterpart CN application No. 201280023326.5; w/English translation (total 17 pages).
(Continued)

*Primary Examiner* — Philip R Wiest
(74) *Attorney, Agent, or Firm* — Westerman, Hattori, Daniels & Adrian, LLP

(57) ABSTRACT

A container for a solid product for dialysis has a connector (200) for connection to a dialysis machine, with a filling channel (202) that crosses it from one end to the other for filling the receptacle with solid product; a fluid line (211, 212, 213) for introducing a solution-making liquid, extending between a first connecting portion (211) that opens to the outside and an orifice (213) that opens to the inside; and a fluid line (221, 222, 223, 224) for extracting the obtained
(Continued)

Figure 1A:
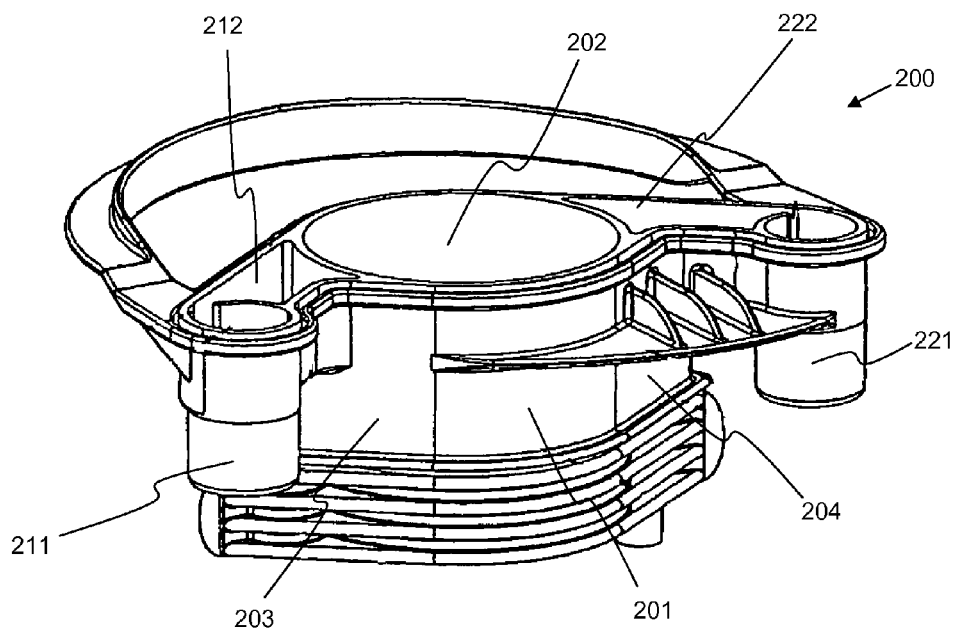

solution, extending between a second connecting portion (221) that opens to the outside and an orifice (224) that opens to the inside. The filling channel (202) is open at both ends and the two fluid lines (211, 212, 213; 221, 222, 223, 224) are fluid-tight between the orifice (213, 224) that opens into the receptacle and the first or second connecting portion (221, 221), respectively.

20 Claims, 4 Drawing Sheets

(51) Int. Cl.
*A61J 1/14* (2006.01)
*A61M 1/16* (2006.01)
*A61J 1/10* (2006.01)

(52) U.S. Cl.
CPC ........ *A61M 1/1656* (2013.01); *A61M 1/1668* (2014.02); *A61J 1/10* (2013.01); *A61J 1/1425* (2015.05); *Y10T 29/49826* (2015.01)

(58) Field of Classification Search
USPC .................................................. 604/403–416
See application file for complete search history.

(56) References Cited

U.S. PATENT DOCUMENTS

| | | |
|---|---|---|
| 4,396,383 A | 8/1983 | Hart |
| 4,415,393 A | 11/1983 | Grimes |
| 4,489,535 A | 12/1984 | Veltman |
| 4,515,586 A | 5/1985 | Mendenhall et al. |
| 4,519,499 A | 5/1985 | Stone et al. |
| 4,561,110 A | 12/1985 | Herbert |
| 4,606,734 A | 8/1986 | Larkin et al. |
| 4,614,515 A | 9/1986 | Tripp et al. |
| 4,781,679 A | 11/1988 | Larkin |
| 5,084,040 A | 1/1992 | Sutter |
| 5,364,384 A | 11/1994 | Grabenkort et al. |
| 5,385,564 A | 1/1995 | Slater et al. |
| 5,766,147 A | 6/1998 | Sancoff et al. |
| 6,645,191 B1 | 11/2003 | Knerr et al. |
| 6,663,743 B1 | 12/2003 | Becker et al. |
| 7,223,262 B2 | 5/2007 | Brehm et al. |
| 8,215,481 B1 | 7/2012 | Knickerbocker |
| 8,479,943 B2 | 7/2013 | Wilhelm |
| 9,029,333 B2 | 5/2015 | Sugiyama et al. |
| 2002/0012707 A1 | 1/2002 | Duponchelle et al. |
| 2003/0012714 A1 | 1/2003 | Taylor |
| 2003/0168120 A1* | 9/2003 | Brehm ................ A61M 1/1656 141/313 |
| 2004/0104247 A1 | 6/2004 | Anderson |
| 2004/0186408 A1 | 9/2004 | Behague et al. |
| 2005/0096625 A1 | 5/2005 | Brandl et al. |
| 2005/0161348 A1 | 7/2005 | Morini |
| 2005/0205438 A1 | 9/2005 | Hierzer et al. |
| 2005/0215943 A1 | 9/2005 | Brandenburger et al. |
| 2005/0279653 A1 | 12/2005 | Williams-Lucas et al. |
| 2006/0172954 A1 | 8/2006 | Jensen et al. |
| 2006/0210739 A1 | 9/2006 | Loffler et al. |
| 2007/0003637 A1 | 1/2007 | Elisabettini et al. |
| 2007/0225673 A1 | 9/2007 | Brehm et al. |
| 2008/0009783 A1 | 1/2008 | Branderburger et al. |
| 2008/0093326 A1 | 4/2008 | Cho |
| 2009/0139951 A1 | 6/2009 | Chen |
| 2010/0069817 A1 | 3/2010 | Falkvall et al. |
| 2010/0120702 A1 | 5/2010 | Sugiyama et al. |
| 2010/0163442 A1 | 7/2010 | Lee et al. |
| 2011/0120302 A1 | 5/2011 | Raiford et al. |
| 2011/0137280 A1 | 6/2011 | Ramella et al. |
| 2011/0266171 A1 | 11/2011 | Rovelli |
| 2013/0183389 A1 | 7/2013 | Carlsson et al. |
| 2013/0190681 A1 | 7/2013 | Jansson et al. |
| 2014/0144794 A1 | 5/2014 | Eyrard et al. |

FOREIGN PATENT DOCUMENTS

| | | |
|---|---|---|
| CN | 101427978 A | 5/2009 |
| CN | 102143773 A | 8/2011 |
| EP | 0395758 A1 | 11/1990 |
| EP | 1344550 A1 | 9/2003 |
| EP | 1572551 A1 | 1/2004 |
| EP | 1642614 A1 | 4/2006 |
| EP | 1710169 A1 | 10/2006 |
| EP | 2585076 B1 | 3/2015 |
| FR | 1154323 A | 4/1958 |
| GB | 2317870 A | 4/1998 |
| JP | S58-169466 A | 10/1983 |
| JP | S58-501757 A | 10/1983 |
| JP | 2001-340423 A | 12/2001 |
| JP | 2003-275299 A | 9/2003 |
| JP | 2005-514283 A | 5/2005 |
| JP | 2005-527301 A | 9/2005 |
| JP | 2006-521124 A | 9/2006 |
| JP | 2009-518252 A | 5/2009 |
| WO | 83/01416 A1 | 4/1983 |
| WO | 89/02730 A1 | 4/1989 |
| WO | 96/40327 A | 12/1996 |
| WO | 2004/005154 A1 | 1/2004 |

OTHER PUBLICATIONS

Japanese Office Action dated Feb. 16, 2016 issued in counterpart JP application No. 2014-510755; w/English translation (total 7 pages).
International Search Report of PCT/EP2012/058829, mailing date of Jul. 30, 2012.
Japanese Office Action (Notice of Allowance) dated Jul. 12, 2016 issued in corresponding Japanese application No. 2014-510755; with English machine translation (6 pages) (documents D1-D4 cited in the Japanese Office Action are not listed since they are already of record).
International Search Report dated Nov. 23, 2012, issued in corresponding application No. PCT/EP2012/065481 of co-pending U.S. Appl. No. 14/233,528; in English (4 pages).
Chinese Office Action dated Aug. 13, 2015 in corresponding Chinese application No. 201280036464.7; with English translation (9 pages).
Japanese Office Action dated Mar. 1, 2016 in corresponding Japanese application No. 2014-524367 of counterpart U.S. Appl. No. 14/233,528; with English translation (4 pages).
Office Action dated Mar. 9, 2016 in co-pending U.S. Appl. No. 14/233,528, with PTO892; without returned SB08 (23 pages).
Office Action dated Jul. 25, 2016 in co-pending U.S. Appl. No. 14/233,528; with PTO892; without amended abstract (24 pages).
Final Office Action dated Nov. 2, 2016 in co-pending U.S. Appl. No. 14/233,528; without returned sb08 (27 pages).

* cited by examiner

Fig. 2
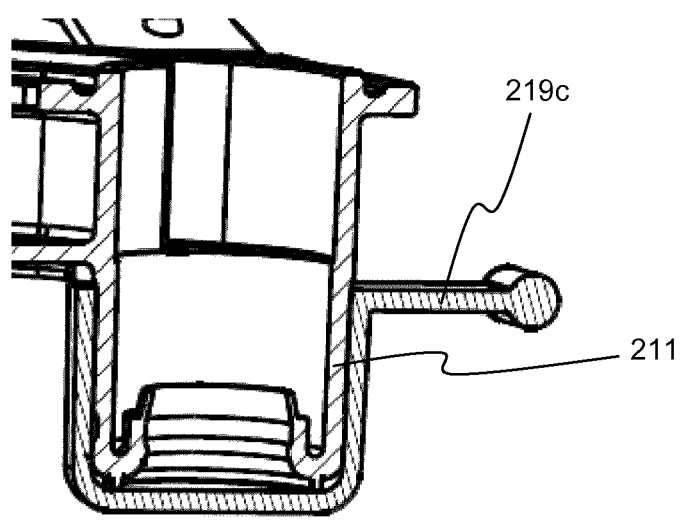
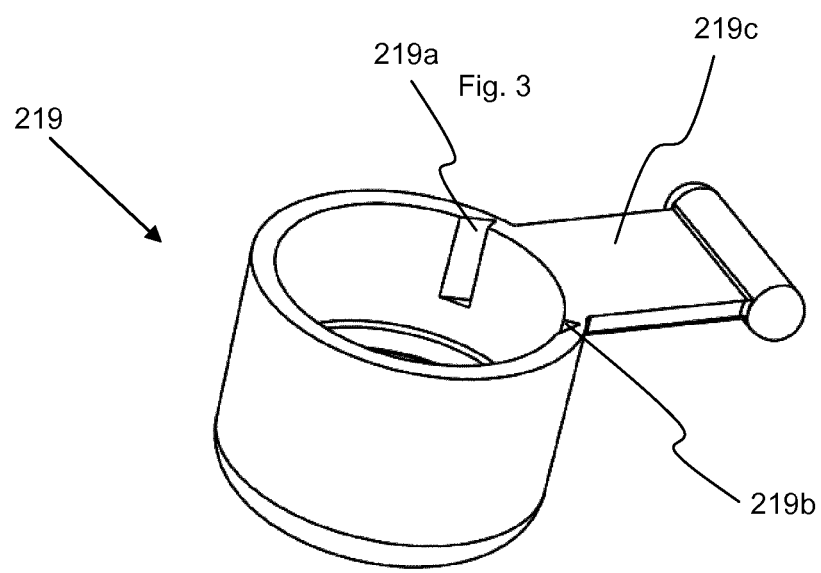
Fig. 3

CONNECTOR FOR DIALYSIS CONTAINER, CONTAINER EQUIPPED WITH SUCH CONNECTOR, MANUFACTURING AND FILLING METHOD FOR SUCH CONNECTORS AND CONTAINERS

The invention concerns a container formed by a receptacle intended to contain a solid product and a connector for connecting the receptacle to a dialysis machine, the connector being equipped with a filling channel that crosses it from one end to the other and enables filling the receptacle with the solid product, a fluid line for introducing a solution-making liquid, which fluid line extends between a first connecting portion that opens to the outside of the receptacle and an orifice that opens to the inside the receptacle, and a fluid line for extracting the obtained solution from the receptacle, which fluid line extends between a second connecting portion that opens to the outside of the receptacle and an orifice that opens to the inside the receptacle, the first connecting portion and the second connecting portion serving as means for connecting the corresponding fluid lines to the dialysis machine. The invention also concerns a connector for such a container and a method of manufacturing such containers and connectors and a method for filling such containers.

Most hemodialysis apparatuses used for routine treatments prepare the fluid required for the dialysis themselves, in a preparation module included in the apparatus. To this effect, the module dilutes, to the appropriate concentration, a saturated solution which is either contained in cans or prepared in a solution-making module also included in the machine. With such solution-making modules, it is no longer necessary to carry cans to the machine, but only containers containing the dialysis product in solid form, generally, sodium bicarbonate. This makes it possible to reduce considerably shipping and storage costs as well as loads manipulated by the staff.

There are different types of containers for these solution-making modules. For example, the containers described in documents EP 1 344 550 A1 and EP 1 642 614 A1 can be mentioned. These containers are constituted by a connector on which is welded a receptacle having the shape of a flexible pouch or a cartridge. The connector is equipped with a first fluid line that makes it possible to introduce water into the receptacle and a second fluid line that makes it possible to extract the saturated solution thus obtained from the receptacle. The first fluid line comprises a first vertical hollow cylindrical connecting portion designed to penetrate via its lower end into a corresponding port of the solution-making module of the dialysis machine. This hollow connecting portion is extended by a first transverse channel which is itself extended by a first downward channel which opens into the receptacle. Similarly, the second fluid line comprises a second vertical hollow cylindrical connecting portion designed to penetrate via its lower end into a corresponding port of the solution-making module of the dialysis machine. This second hollow connecting portion is extended by a second transverse channel which is itself extended by a second downward channel to which is connected a pickup tube that opens at the bottom of the receptacle. Additionally, the connector is crossed by a large central channel which makes it possible to fill the receptacle with solid product.

The channels that cross the cylindrical connecting portions and the downward channels are substantially vertical, whereas the transverse channels that connect them are substantially horizontal. Before filling up, the upper parts of these transverse channels are open. These upper parts are located in a same plane as the upper edge of the central filling channel and the upper edge of the hollow cylindrical connecting portions.

It is thus necessary to provide a site to manufacture a container, site in which a pouch or a cartridge is welded to a connector whose filling channel and transverse channels are open at their upper part, then a site to fill the container with dialysis product. It is at that site, at the end of the filling procedure, that a flexible film is welded to the upper edge of the connector. Closing the filling channel with such a film has the advantage of guaranteeing the originality of the closure: any attempt at manipulating the content will result in a well-visible rupture of the film. This film is welded, on the one hand, to the upper edge of the filling channel, so as to close the container. On the other hand, it is welded to the upper edges of the lower wall of the transverse channels and to the edge of the upper end of the cylindrical connecting portions, thus forming the upper wall of the transverse channels. The positioning and welding of the film complicate substantially the filling procedure, because they require cleaning the welding zone to remove any trace of dust, especially the dust caused by the filling procedure. As a result, there are usually only a few filling sites, from where the filled containers are then distributed throughout the whole world.

Thus, an objective of the invention is to develop a container and a connector according to the preamble so that it is possible to manufacture empty containers at a site and fill them at other sites without having to resort to welding to close the filled container.

This objective is reached according to the invention with a container in which the filling channel is open at both ends and in that the two fluid lines are fluid-tight between the orifice that opens into the receptacle and the first or second connecting portion, respectively. After filling, the filling channel can be closed with a plug. It is thus possible to manufacture empty containers in a specialized and well-equipped site. The welding unit can close the top of the transverse channels while leaving the filling orifice open for a future filling procedure. These empty containers are sent to filling sites distributed throughout the whole world and close to the final users. These sites do not need to be equipped with a welding unit.

It is preferable to provide that the fluid line for introducing the solution-making liquid is constituted by a first channel that crosses the first connecting portion and is extended by a first transverse channel, then by a first downward channel that opens to the inside of the receptacle by an orifice, the first cylindrical connecting portion and the first downward channel being substantially parallel to the filling channel and diverging from the first transverse channel in the same direction. Similarly, it can be provided that the fluid line for extracting the obtained solution is constituted by a second channel that crosses the second connecting portion and is extended by a second transverse channel, then by a second downward channel that opens to the inside of the receptacle by an orifice, the second cylindrical connecting portion and the second downward channel being substantially parallel to the filling channel and diverging from the second transverse channel in the same direction.

As in documents EP 1 344 550 A1 and EP 1 642 614 A1, it can be provided that the first transverse channel is constituted by an upper wall located in the plane defined by the upper end of the filling channel and a complementary wall, said upper wall being constituted by a flexible film welded to the upper edge of the first connecting portion, to the upper edges of the complementary wall and to the portion of the upper edge of the filling channel adjacent to the first transverse channel. Similarly, it can be provided that the second transverse channel is constituted by an upper wall located in the plane defined by the upper end of the filing channel and a complementary wall, said complementary wall being constituted by a flexible film welded to the upper edge of the second connecting portion, to the upper edges of the complementary wall and to the portion of the upper edge of the filling channel adjacent to the second transverse channel. Contrary to the containers of documents EP 1 344 550 A1 and EP 1 642 614 A1, it is thus possible to weld flexible films forming the upper walls of the transverse channels during the manufacture of the containers, or even during the manufacture of the connectors before they are equipped with a receptacle, i.e., before filling. At that time, there are no problems of dust caused by filling. As a result, containers that are very close to those of documents EP 1 344 550 A1 and EP 1 642 614 A1 can be used, without having to perform welding on the filling site.

In order to facilitate welding of the receptacle on the connector, the latter can be equipped with two fins placed on the outside face of the wall that forms the filling channel, opposite to each other. Seen from above, this portion of the connector has the shape of an elongated rhombus with rounded median angles.

The connecting portions of the fluid line for introducing the solution-making liquid and the fluid line for extracting the obtained solution can be closed by a welded flexible film, as in the state of the art. However, in a variant embodiment of the invention, they are closed by lids that cannot be removed without destruction. In order to facilitate their removal at the time of use, it is preferable to equip them with weakness zones that facilitate their voluntary destruction. These weakness zones can be constituted by two notches provided in the thickness of the wall of the lids in a direction away from the orifice of introduction of the said lids, and a tongue can be placed in the vicinity of this introduction orifice, between the two notches. At the time of use, it is possible to tear apart the lid in the area of the two notches by pulling on the tongue, and to remove the lid thus destroyed.

The invention also concerns a connector having the characteristics mentioned above.

It also concerns a method of manufacturing a container or a connector according to the invention, comprising the following steps:
(a) manufacturing a connector equipped with
  a filling channel that crosses it from one end to the other;
  a fluid line for introducing a solution-making liquid, which fluid line extends between a first connecting portion that opens to the outside of the receptacle, when such a receptacle is fixed to the connector, and an orifice that opens to the inside of the receptacle, a section of this fluid line located between the first connecting portion and the orifice that opens to the inside of the receptacle being open; and
  a fluid line for extracting the obtained solution, which fluid line extends between a second connecting portion that opens to the outside of the receptacle, when such a receptacle is fixed to the connector, and an orifice that opens to the inside of the receptacle, a section of this fluid line located between the second connecting portion and the orifice that opens to the inside of the receptacle being open,
(b) sealing the orifices of the sections of the fluid lines in a fluid-tight manner so that the two fluid lines are fluid-tight between the orifice that opens to the inside the receptacle and the first or second connecting portion, respectively.

The manufacturing method of the invention is characterized in that, at step (b), the filling channel is left open at both ends. In order to manufacture a container from this connector, it is possible to attach a receptacle to this connector.

The invention also concerns a method of filling a container according to the invention. This method is characterized by the following steps:
(a) filling the container via the filling channel;
(b) sealing the filling channel in a fluid-tight manner.

The sealing of step (b) can be performed easily by introducing a plug into the filling channel.

Figure 1B:
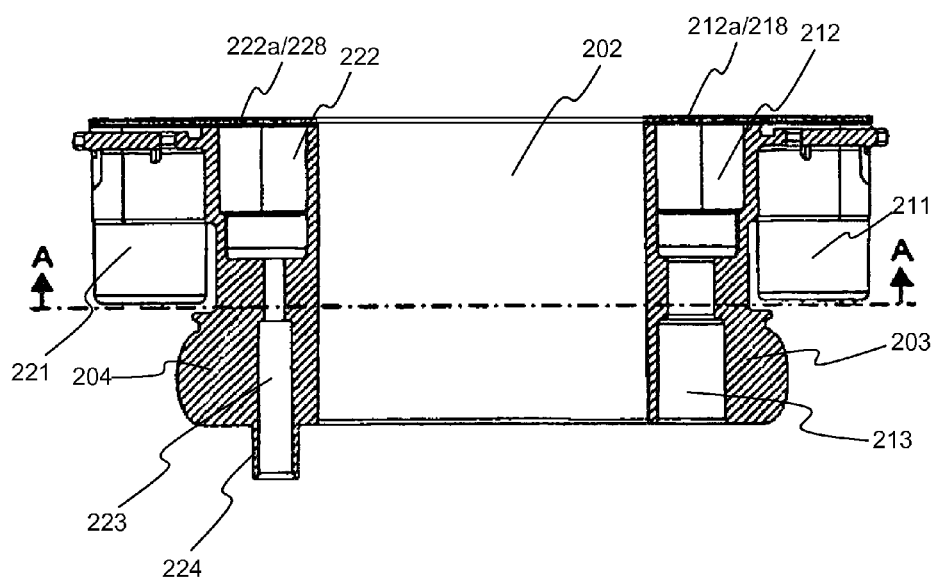
Figure 1C:
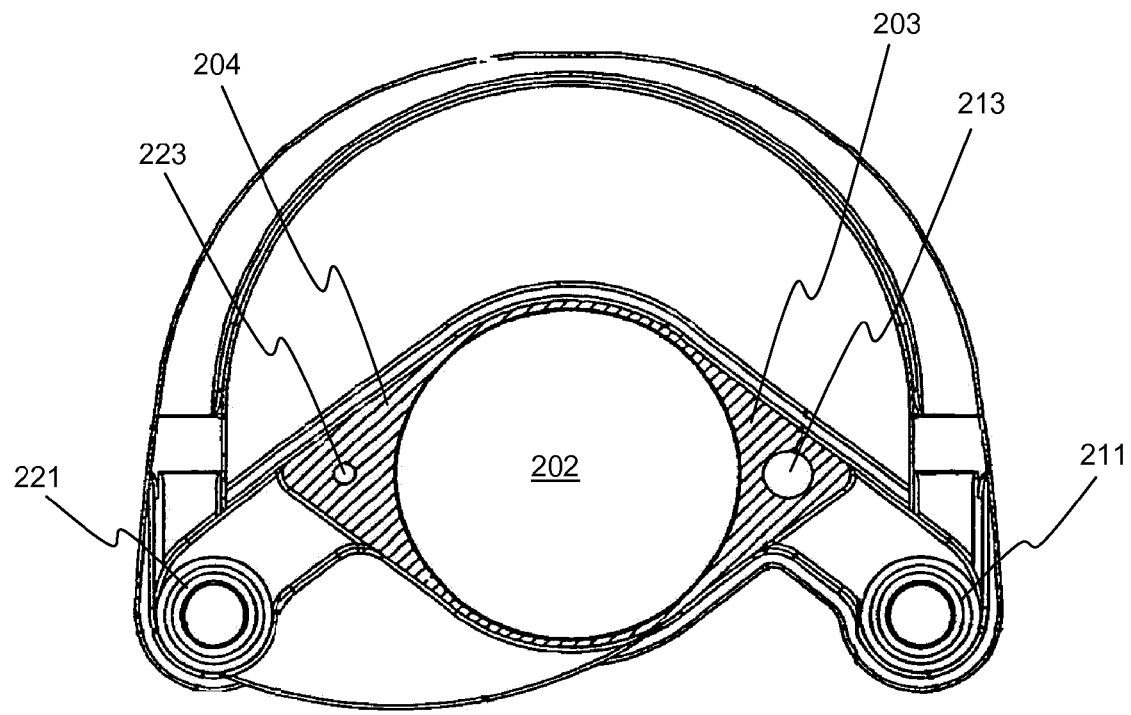

The invention is described in more details below in reference to the following Figures:

FIG. 1: (a) perspective view, (b) vertical cross-sectional view across the filling orifice and the fins, and (c) horizontal cross-sectional view (along line A-A of Figure b) of a connector whose filling orifice is open;

FIG. 2: cross-sectional partial view of the connector of FIG. 1 in the area of a cylindrical connecting portion, which is closed by a closing lid;

FIG. 3: perspective view of a closing lid for a cylindrical connecting portion.

Figure 4:
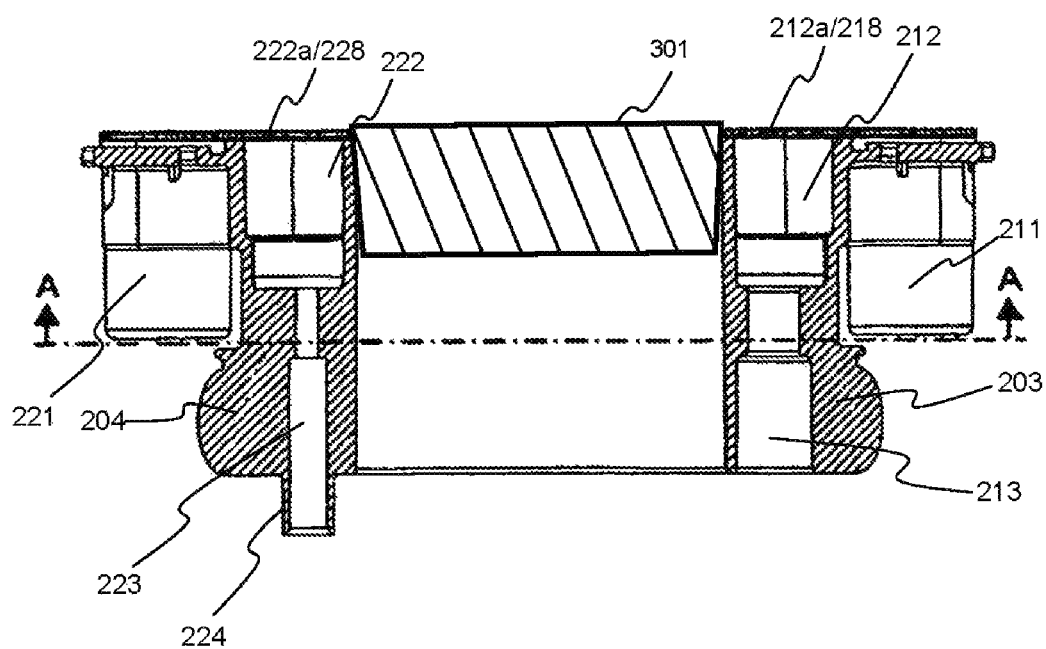

FIG. 4: vertical cross-sectional view corresponding to FIG. 1b, with a plug closing the filling channel.

The invention relates to a connector (200) designed to be equipped with a receptacle not shown, as well as to the container constituted by a connector (200) equipped with the receptacle. The invention also relates to the method of manufacture of such a connector and such a container, as well as to the method of filling such a container. When the connector is considered alone, the ends of its various channels do not open to the inside or to the outside of the container since it is not yet equipped with a receptacle. However, the positions of the various parts of the connector are indicated by analogy with the container obtained by welding a receptacle to the connector.

In the example of embodiment presented in this application, the connector (200) corresponds substantially to those described in documents EP 1 344 550 A1 and EP 1 642 614 A1. They are generally welded at the top of cartridges or pouches intended to receive a solid product in the form of a powder or granules for dialysis. During use, the connector is connected to a machine which introduces water into the cartridge, then aspirates the water saturated with the product. The product is usually sodium bicarbonate.

Such connectors comprise essentially:
  a central hollow cylinder (201) crossed from one end to the other by a central filling channel (202) open at both ends and intended for filling the pouch or cartridge with solid product;
  two fins (203, 204) disposed on opposite sides of the central cylinder to facilitate welding of the pouch or cartridge on the connector;
  a first fluid line, or filling line, constituted by a first connection channel that crosses a first hollow cylindrical connecting portion (211) that opens to the outside of the receptacle, the first connection channel being extended by a first transverse channel (212), then by a first downward channel (213) that opens to the inside of the receptacle via an orifice, this first downward channel being substantially parallel to the filling channel (202) and located inside the first fin (203);
  a second fluid line, or suction line, constituted by a second connection channel that crosses a second hollow cylindrical connecting portion (221) that opens to the outside of the receptacle, the second connection channel being extended by a second transverse channel (222), then by a second downward channel (223), substantially parallel to the filling channel (202) and located inside the second fin (204). This second downward channel (223) is extended by a connecting portion (224) that protrudes below the lower face of the central cylinder (201) and on which a pick-up tube that dips down to the bottom of the pouch can be fixed.

The first and second cylindrical connecting portions (211, 221) are preferably coaxial with the central cylinder (201). They serve to connect the container to the dialysis machine via the fluid lines and they are designed to penetrate via their lower ends into corresponding ports of the dialysis machine. As shown on FIG. 1 *c*, they are located on a same side of a median plane passing through the axis of the filling channel (202) and the fins (203, 204).

The first and second lateral channels (212, 222) are located in a plane perpendicular to the axis of the central cylinder (201). They are each constituted by an upper wall (212*a*, 222*a*) located in the plane defined by the upper end of the filling channel (202) and the upper end of the cylindrical connecting portions (211, 221), and a complementary wall. For cost-saving reasons, and to simplify the manufacture of the connectors, these upper walls (212*a*, 222*a*) are manufactured by welding a flexible film (218, 228) to the upper edge of the cylindrical connecting portions (211, 221), the upper edges of the complementary walls, and the portion of the upper edge of the filling channel (202) adjacent to the transverse channel considered. Contrary to the connectors of documents EP 1 344 550 A1 and EP 1 642 614 B1, the flexible film does not close the upper opening of the filling channel (202). A flexible film is welded to the upper face of each transverse channel. This film is thus welded, on the one hand, to the upper edges of the complementary wall of the transverse channel (212, 222), the upper edge of the corresponding connecting portion (211, 221), and the upper edge of the filling channel, but only in its portion adjacent to the transverse channel considered. It is to be noted that the connecting portion (211, 221) is designed to leave a passage between the connection channel that crosses it and the corresponding transverse channel, so that welding the film to the upper edge of the connector does not obstruct the fluid line. Thus, the fluid line obtained (211, 212, 212*a*, 213; 221, 222, 222*a*, 223, 224) extends between a first connecting portion (211, 221) that opens to the outside of the receptacle and an orifice (213, 224) that opens to the inside of the receptacle, while being fluid-tight between the connecting portion (211, 221) and the inside orifice (213, 224). Thus, the connector and the container of the invention differ from those of the state of the art by the fact that the two transverse channels are already formed before the filling step, whereas the filling channel is still open.

The connector (200) thus formed, with the orifice of the filling channel (202) being open but the lateral channel (212, 222) being formed, is welded at the top of a cartridge or a pouch. The containers thus formed are ready to be sent to the filling sites.

In a conventional manner, filling is performed by introducing the solid product via the central channel (202). The only remaining procedure is to seal the filling orifice, for example, with a plug.

Contrary to the state of the art, sealing of the filled container does not need to be performed by welding a flexible film to the upper edge of the central channel (201). In a preferred embodiment of the invention, this sealing is performed by introducing a plug (301).

After filling the container, the plug is introduced into the filling channel (202).

The lower orifices of the cylindrical connecting portions (211, 221) must be closed in a fluid-tight manner until the connector is introduced into the dialysis machine. In documents EP 1 344 550 A1 and EP 1 642 614 B1, they are closed by a flexible film welded to their periphery. In the containers according to the invention, it is also possible to close these orifices by welding a flexible film during manufacture of the connectors or of the empty containers. However, in a variant embodiment of the invention, the lower ends of these connecting portions (211, 221) can be closed by lids (219) which are equipped, on the one hand, with means for preventing their removal, and on the other hand, with rupturing means which, when they are destroyed, make it possible to extract the lids without damaging the connector. The retaining means can be constituted, for example, by a shoulder which could snaps into a corresponding groove of the connector (or vice versa). The rupturing means can be constituted by weakness points, such as two vertical notches (219*a*, 219*b*) provided in a significant portion of the thickness of the lid. In order to facilitate rupturing the rupturing means, in particular tearing off the notches (219*a*, 219*b*), a tongue (219*c*) can be provided between the two notches, flush with the orifice for introduction of the lid.

Usually, the containers are manufactured by welding the pouches or the cartridges on the connectors. These containers are then delivered to the filling unit. The solid product is introduced into the container via the filling channel (202). The filling dust is eliminated from the upper edges of the central cylinder (201), the lateral walls of the transverse channels (212, 222) and the cylindrical connecting portions (211, 221). Finally, the upper orifice of the filling channel (202) is closed and the upper walls of the transverse channels are formed by welding a flexible film to the edges after having cleaned them. Thanks to the invention, it is no longer necessary to have a particular welding unit at the filling location. It is sufficient to position the plug in the orifice of the channel. The orifices of the cylindrical connecting portions (211, 221) can be closed by a flexible film during manufacture of the connector, or by a lid (219), either during manufacture of the connector or of the container, or during filling.

Welding of the films on the transverse channels is performed before filling: thus, no dust problem arises. The reject rate can thus be reduced.

It is thus possible to manufacture, at a central site, containers with an open filling channel, and then deliver them empty throughout the whole world to filling sites close to clients. As a result, it is possible to reduce transportation costs considerably in-so-far the empty containers, possibly accompanied by their plug not yet introduced into the filling channel, are shipped throughout the whole world from a centralized manufacturing site, whereas the filled and closed containers travel only over much shorter distances between the filling sites and the sites of use.

LIST OF REFERENCES

200 Connector
201 Hollow central cylinder
201 Filling channel
203 Fin
204 Fin
211 First cylindrical connecting portion
212 First transverse channel
212*a* Upper wall of the first transverse channel 213 First downward channel
218 Flexible film constituting the upper wall of the first transverse channel
219 Lid
219a Notch
219b Notch
219c Tongue
221 Second cylindrical connecting portion
222 Second transverse channel
222a Upper wall of the second transverse channel
223 Second downward channel
224 Connecting portion for pick-up tube
228 Flexible film constituting the upper wall of the second transverse channel

The invention claimed is:

1. Container constituted by a receptacle intended for containing a solid product for dialysis and a connector for connecting the receptacle to a dialysis machine, the connector being equipped with
   a filling channel, wherein the filling channel crosses the connector from a first end of the connector to a second end of the connector opposite the first end, and enables filling the receptacle with a solid product;
   a first fluid line for introducing a solution-making liquid into the receptacle, said first fluid line extending between a first connecting portion that opens to an outside of the receptacle and a first orifice that opens to an inside of the receptacle; and
   a second fluid line for extracting an obtained solution from the receptacle, said second fluid line extending between a second connecting portion that opens to the outside of the receptacle and a second orifice that opens to the inside of the receptacle,
   the first connecting portion and the second connecting portion being configured for connecting the corresponding fluid lines to a dialysis machine,
   wherein the filling channel is open at both the first and second ends and each of the two first and second fluid lines is fluid-tight between the first or second orifice that opens into the receptacle, respectively, and the first or second connecting portion, respectively.

2. Container according to claim 1, further comprising a plug configured to be introduced into the filling channel so as to close the filling channel.

3. Container according to claim 1, wherein at least one of
   the first fluid line for introducing the solution-making liquid is constituted by a first channel that crosses the first connecting portion and is extended by a first transverse channel, then by a first downward channel that opens to the inside the receptacle via the first orifice, the first connecting portion and the first downward channel being substantially parallel to the filling channel and diverging from the first transverse channel in the same direction, and
   the second fluid line for extracting the obtained solution is constituted by a second channel that crosses the second connecting portion and is extended by a second transverse channel, then by a second downward channel that opens to the inside the receptacle via the second orifice, the second connecting portion and the second downward channel being substantially parallel to the filling channel and diverging from the second transverse channel in the same direction.

4. Container according to claim 3, wherein at least one of
   the first transverse channel is constituted by an upper wall located in a plane defined by an upper end of the filling channel and a complementary wall, said upper wall being constituted by a flexible film welded to an upper edge of the first channel, upper edges of the complementary wall, and a portion of the upper edge of the filling channel adjacent to the first transverse channel, and
   the second transverse channel is constituted by an upper wall located in a plane defined by an upper edge of the filling channel and a complementary wall, said upper wall being constituted by a flexible film welded to an upper edge of the second channel, upper edges of the complementary wall, and a portion of the upper edge of the filling channel adjacent to the second transverse channel.

5. Container according to claim 1, wherein the connector is equipped with two fins placed on an outside face of a wall forming the filling channel, opposite to each other.

6. Container according to claim 1, wherein the connecting portions are obstructed by lids that are impossible to remove without destroying them.

7. Container according to claim 6, wherein the lids are equipped with weakness zones that facilitate their voluntary destruction.

8. Container according to claim 7, wherein the weakness zones are constituted by two notches provided in a thickness of the wall of the lids in a direction away from an introduction orifice for introduction of said lids, a tongue being placed in a vicinity of the introduction orifice between the two notches.

9. Connector for connecting a receptacle intended for containing a solid product for dialysis to a dialysis machine, said connector being equipped with
   a filling channel, wherein the filling channel crosses the connector from a first end of the connector to a second end of the connector opposite the first end, and enables filling a receptacle with a solid product, when such a receptacle is fixed on the connector;
   a first fluid line for introducing a solution-making liquid into the receptacle, said first fluid line extending between a first connecting portion that opens to an outside of the receptacle, when such a receptacle is fixed on the connector, and a first orifice that opens to the inside of the receptacle; and
   a second fluid line for extracting an obtained solution from the receptacle, said second fluid line extending between a second connecting portion that opens to the outside of the receptacle, when such a receptacle is fixed on the connector, and a second orifice that opens to the inside of the receptacle,
   the first connecting portion and the second connecting portion being configured for connecting the corresponding fluid lines to a dialysis machine,
   wherein the filling channel is open at both the first and second ends and each of the first and second fluid lines is fluid-tight between the first or second orifice that opens into the receptacle, respectively, and the first or second connecting portion, respectively.

10. Connector according to claim 9, wherein at least one of
    the first fluid line for introducing the solution-making liquid is constituted by a first channel that crosses the first connecting portion and is extended by a first transverse channel, then by a first downward channel that opens to the inside the receptacle via the first orifice, the first connecting portion and the first downward channel being parallel to the filling channel and diverging from the first transverse channel in the same direction, and the second fluid line for extracting the obtained solution is constituted by a second channel that crosses the first connecting portion and is extended by a second transverse channel, then by a second downward channel that opens to the inside of the receptacle via the second orifice, the second connecting portion and the second downward channel being parallel to the filling channel and diverging from the second transverse channel in the same direction.

11. Connector according to claim 10, wherein at least one of the first transverse channel is constituted by an upper wall located in a plane defined by an upper end of the filling channel and a complementary wall, said upper wall being constituted by a flexible film welded to an upper edge of the first channel, upper edges of the complementary wall, and a portion of the upper edge of the filling channel adjacent to the transverse channel, and the second transverse channel is constituted by an upper wall located in a plane defined by an upper edge of the filling channel and a complementary wall, said upper wall being constituted by a flexible film welded to an upper edge of the second channel, upper edges of the complementary wall, and the portion of the upper edge of the filling channel adjacent to the transverse channel.

12. Method of manufacturing a connector, comprising:
(a) manufacturing a connector equipped with
  a filling channel which crosses the connector from a first end of the connector to a second end of the connector opposite the first end;
  a first fluid line for introducing a solution-making liquid, said first fluid line extending between a first connecting portion that opens to an outside of the receptacle, when a receptacle is fixed on the connector, and a first orifice that opens to an inside of the receptacle, a first section of the first fluid line located between the first connecting portion and the first orifice that opens to the inside of the receptacle being open; and
  a second fluid line for extracting an obtained solution, said second fluid line extending between a second connecting portion that opens to the outside of the receptacle, when a receptacle is fixed on the connector, and a second orifice that opens to the inside of the receptacle, a second section of the second fluid line located between the second connecting portion and the second orifice that opens to the inside of the receptacle being open,
(b) sealing the first and second sections of the fluid lines in a fluid-tight manner so that each of the first and second fluid lines is fluid-tight between the first or second orifice that opens into the receptacle, respectively, and the first or second connecting portion, respectively,
  wherein, in step (b), the filling channel is left open at both the first and second ends, so as to obtain the connector according to claim 9.

13. Method according to claim 12, comprising fixing a receptacle on the connector.

14. Method of filling a container according to claim 1, comprising:
(a) filling the container via the filling channel;
(b) sealing the filling channel in a fluid-tight manner.

15. Method according to claim 14, wherein the sealing (b) is performed by introducing a plug into the filling channel.

16. Container according to claim 2, wherein at least one of the first fluid line for introducing the solution-making liquid is constituted by a first channel that crosses the first connecting portion and is extended by a first transverse channel, then by a first downward channel that opens to the inside the receptacle via the first orifice, the first connecting portion and the first downward channel being substantially parallel to the filling channel and diverging from the first transverse channel in the same direction, and the second fluid line for extracting the obtained solution is constituted by a second channel that crosses the second connecting portion and is extended by a second transverse channel, then by a second downward channel that opens to the inside the receptacle via the second orifice, the second connecting portion and the second downward channel being substantially parallel to the filling channel and diverging from the second transverse channel in the same direction.

17. Container according to claim 16, wherein at least one of the first transverse channel is constituted by an upper wall located in a plane defined by an upper end of the filling channel and a complementary wall, said upper wall being constituted by a flexible film welded to an upper edge of the first channel, upper edges of the complementary wall, and a portion of the upper edge of the filling channel adjacent to the first transverse channel, and the second transverse channel is constituted by an upper wall located in a plane defined by an upper edge of the filling channel and a complementary wall, said upper wall being constituted by a flexible film welded to an upper edge of the second channel, upper edges of the complementary wall, and a portion of the upper edge of the filling channel adjacent to the second transverse channel.

18. Container according to claim 2, wherein the connector is equipped with two fins placed on an outside face of a wall forming the filling channel, opposite to each other.

19. Container according to claim 3, wherein the connector is equipped with two fins placed on an outside face of a wall forming the filling channel, opposite to each other.

20. Container according to claim 4, wherein the connector is equipped with two fins placed on an outside face of a wall forming the filling channel, opposite to each other.

* * * * *